United States Patent [19]

Bauerle

[11] 4,392,388

[45] Jul. 12, 1983

[54] GAS SAMPLER FOR AEROSOL ATMOSPHERE

[75] Inventor: James E. Bauerle, Plum Borough, Pa.

[73] Assignee: Westinghouse Electric Corp., Pittsburgh, Pa.

[21] Appl. No.: 235,208

[22] Filed: Feb. 17, 1981

[51] Int. Cl.³ .............................................. G01N 1/26
[52] U.S. Cl. .................................... 73/863.23; 55/158
[58] Field of Search ................. 73/863.21, 863.23, 19, 73/863.41; 55/158, 270, 16, 17

[56] References Cited

U.S. PATENT DOCUMENTS

| | | | |
|---|---|---|---|
| 2,771,158 | 11/1956 | Bray . | |
| 3,421,292 | 1/1965 | Llewellyn | 55/158 |
| 3,494,174 | 2/1970 | Green | 55/158 |
| 3,731,464 | 5/1973 | Brumbaugh . | |
| 3,923,461 | 12/1975 | Barden | 55/158 |
| 3,926,561 | 12/1975 | Lucero | 55/158 |
| 3,973,928 | 8/1976 | Nierenberg | 55/158 |
| 4,019,863 | 4/1977 | Jenkins . | |
| 4,140,005 | 2/1979 | Kittelson . | |
| 4,284,418 | 8/1981 | Andres | 55/16 |

FOREIGN PATENT DOCUMENTS 1222933 2/1971 United Kingdom .
1445061 8/1976 United Kingdom .

Primary Examiner—Charles A. Ruehl
Assistant Examiner—Denis E. Corr
Attorney, Agent, or Firm—Kenneth R. Bowers

[57] ABSTRACT

A process and device using back-diffusion for sampling a gas from an environment containing an aerosol of tramp material. The device cleans the tramp material from a barrier by the flow of a purge gas. The purge gas flow prevents diffusion of the tramp material through ports in the barrier through which the sample gas diffuses against purge gas flow. The purge gas continuously cleans the barrier, retards tramp material diffusion, and gathers and transports the sample gas.

3 Claims, 3 Drawing Figures

GAS SAMPLER FOR AEROSOL ATMOSPHERE

BACKGROUND OF THE INVENTION

This invention relates to a new system for sampling the gas contained in an environment such as the containment building surrounding a sodium-cooled nuclear power reactor, or the stack of an industrial plant. The gas to be sampled may be an elemental species, or may be a mixture of many elements or gaseous compounds. The purpose of obtaining a sample of the gas may be to ascertain the qualitative and quantitative content of the gas for purposes of documentation or control.

In certain environments, the gas to be sampled either contains, or potentially may contain, mixtures, suspensions or aerosols. These terms refer to conditions in which the gas contains solid particles or liquid droplets considered tramp material herein, either dissolved, suspended, or merely mixed in the gas.

The solid matter may range greatly in size. Encompassed in the term "tramp material" herein are particles of solid matter as large as ashes commonly contained in stack gas, or as small as smoke or dust particles. The tramp material contained in the gas may interfere with the sampling process in a variety of ways. The sample lines may become plugged, or require frequent servicing. The tramp material may be radioactive, posing an obstacle to radiation measurements of the gas.

The exclusion of solid tramp material from the sample might be accomplished by filters. This is not, however, suitable for some ranges of tramp material size and concentration. Very small particles may pass through a filter of a given mesh while a very large concentration of tramp material could rapidly clog or saturate a filter.

A particular sampling problem could arise following a coolant leak in the piping of a sodium-cooled reactor. The sodium concentration in the containment building gas, in the form of an aerosol, could then be very high, precisely when the sampling need may be most important.

It is desired to provide a sampler which can sample a gas containing tramp material without degraded performance.

SUMMARY OF THE INVENTION

The invention is a reliable sampling process and device which is adapted to exclude tramp material even when such material is present in the gas in high concentrations. The process utilizes a differential in diffusion rates of the gas and the tramp material to accomplish the desired sampling of the gas and exclusion of the tramp material.

The environment to be sampled has introduced therein a first surface of a barrier which has one or a plurality of diffusion ports therethrough to a second surface of the barrier. The barrier may be a solid, aggregated plate whose diffusion ports are holes, drilled or otherwise formed. Alternatively, the barrier may be a porous or fibrous material, whose natural gas-permeable channels then constitute the diffusion ports. The port diameter is greater than one mean free path of the sample gas molecules to enhance gas diffusion. The second surface of the barrier faces a purge gas stream which flows over this second barrier surface. Some of the purge gas flows through the ports into the sample environment, thereby continuously cleaning the ports. Some of the gas diffuses through the ports (this diffused gas is hereinafter defined as "sample gas") in the barrier into the purge gas flow which gathers the sample gas and transports it to a sampling analyzer. This diffusion is termed "back diffusion" since it occurs through an opposed purge gas flow path.

Some of the tramp material undesirably may also back-diffuse into the purge gas stream. This effect is greatly reduced by the opposed flow of the purge gas through the ports.

An equation for concentration of sample gas ($C_s$) or tramp material ($C_t$) found in the purge gas can be found in W. Jost, *Diffusion in Solids, Liquids, Gases,* Academic Press Inc., New York, 1952, Chapter 10, pp. 410–411.

$$C_{s,t} = C_O \operatorname{EXP}(-VL/D_{s,t}) = C_O F \tag{1}$$

where $C_O$ is the gas concentration, V is the purge gas velocity, L is the port length, and $D_{s,t}$ is the appropriate diffusion coefficient. The exponential term has been characterized as F; the concentration attenuation factor.

The F-factor above is valid for low gas flow rates from the sampler to the analyzer. At high flow rates, appreciable dilution of the sampled gas by the purge gas will occur. A gas flow rate "S" is sufficiently low if it equals or is less than:

$$S \leq D_{s,t} A/L$$

where A is the total diffusion port area.

Proper selection of the purge gas species, purge gas velocity, and port length allows the sampler to be matched to particular sampling situations involving specific tramp material species and gas species in the environment. The preferred embodiment described below will illustrate one application.

DESCRIPTION OF THE PREFERRED EMBODIMENT

The application of the invention to a sodium-cooled nuclear power reactor containment will be described as the preferred embodiment.

Figure 1:
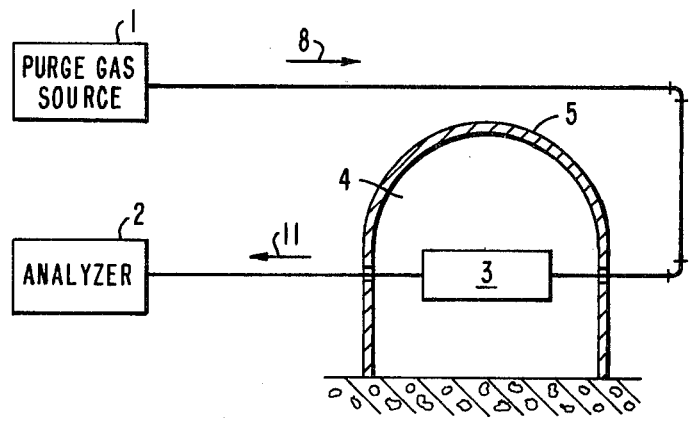
FIG. 1 is a schematic illustrating the general arrangement of the sampler components.

Referring to FIG. 1, a reactor containment building 5 surrounds a reactor (not shown) and a sampler probe 3. The containment building 5 is an environment which contains, or may contain, a variety of gas species. A purge gas source 1 continuously supplys a purge gas flow 8 through a sampler probe 3 to an analyzer 2.

Figure 2:
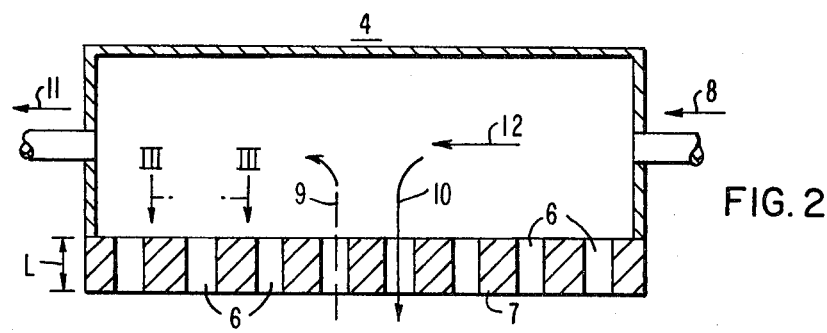
FIG. 2 is a lateral cross section of a preferred embodiment of the sampler probe.

Referring to FIG. 2, a section of the sampler probe 3, it is seen that some of the purge gas flows through ports 6 into the reactor containment volume 4 (arrows 10). During a serious sodium leak, this volume 4 is predicted to contain an aerosol of sodium and sodium reaction products in the gas, said products ranging in diameter from 0.01 μm to 1000 μm and of concentration up to 100 gms/m³. Some of the gas and perhaps some of the sodium aerosol back-diffuses (arrow 9) across a barrier 7 through ports 6 into the purge gas flow 12 inside the sampler probe 3. Here it is swept along with the purge gas flow 12 to the analyzer 2. (Arrow 11)

Figure 3:
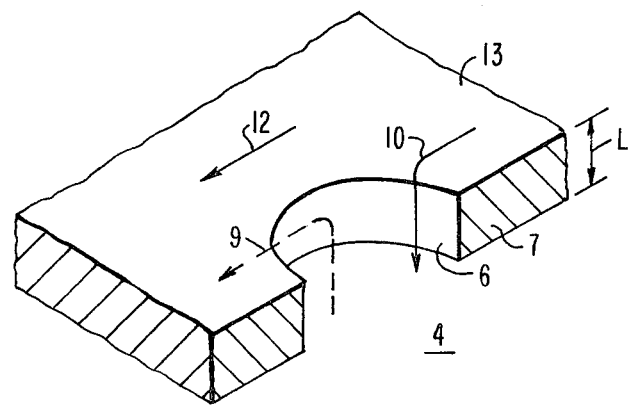
FIG. 3 is a section of the barrier taken as indicated from FIG. 2.

The principle of back-diffusion is illustrated in FIG. 3. The purge gas flow 12 passes over the inner surface 13 of the barrier 7, some of this flow passing through the port 6 into the containment volume 4. (Arrow 10) This flow prevents the plugging of port 6 by tramp material, here the sodium aerosol present in volume 4, and greatly inhibits tramp particle diffusion.

Some of the gas in volume 4 back-diffuses (Arrow 9) through the port 6 and into the purge gas flow 12. For sufficiently low purge gas flow rates, sufficiently small port length (barrier thickness) L, certain sample and purge gas species, and a range of tramp material sizes, it is shown below that the back-diffusion rate of the sample gas greatly exceeds the diffusion of tramp material.

The efficiency of the sampler in sampling the gas and excluding the tramp material is due to the relative diffusion rates of these across barrier 7. The purge gas flow through the ports is thought to inhibit the diffusion of the tramp material through the ports more than the diffusion of the sample gas through the ports because the tramp material particle size is greater than the sample gas particle size.

Concentration attenuation factors F from equation I have been calculated using an arbitrarily chosen purge gas velocity of 1 cm/sec and a port length (barrier thickness) L of 0.1 cm, and are listed in Tables I and II.

TABLE 1

| Sample Gas | Purge Gas | Sample Gas Diffusion Coefficient $D_s$ | Sample Gas Attenuation Factor F |
|---|---|---|---|
| $H_2$ | Ar | .77 cm$^2$/sec | .88 |
| $H_2$ | $N_2$ | .80 | .88 |
| $H_2$ | He | 1.38 | .93 |
| $O_2$ | Ar | .20 | .61 |
| $O_2$ | $N_2$ | .22 | .63 |
| $O_2$ | He | .71 | .87 |

TABLE 2

| Tramp Particle Diameter | Tramp Particle Diffusion Coefficient $D_t$ | $LOG_{10}$ Tramp Particle Concentration Attenuation Factor F |
|---|---|---|
| .01 μm | 5.2 × 10$^{-4}$ cm$^2$/sec | −83 |
| .1 | 6.8 × 10$^{-6}$ | very large, negative |
| 1 | 2.8 × 10$^{-7}$ | " |
| 10 | 2.4 × 10$^{-8}$ | " |
| 100 | 2.4 × 10$^{-9}$ | " |
| 1000 | 2.4 × 10$^{-10}$ | " |
| Larger | Smaller | increasingly large, negative |

The sample gas diffusion coefficients in Table 1 are taken from N. B. Vargaftik, *Tables on the Thermophysical Properties of Liquids and Gases*, John Wiley & Sons, Inc., 1975, Chapter 11. The tramp particle diffusion coefficients in Table 2 are taken from S. K. Friedlander, *Smoke, Dust, and Haze*, John Wiley & Sons, Inc., 1977, Chapter 2, pp. 27-34. The purge gas species used are reasonable choices for actual use in a sodium power reactor and the tramp particle diameters correspond to the particle size range expected during a sodium leak in a sodium power reactor. The sample gas species are those believed to be of special interest in a sodium reactor containment.

Thus, the results in Tables 1 and 2 are indicative of the efficiency of the preferred embodiment in a practical application. The sample gas attenuation factor is large (1.0 is theoretical maximum), indicating that relatively high sample gas diffusion rates occur. The extremely small tramp particle concentration attenuation factors (expressed in Table 2 as a very large, negative $LOG_{10}$.) indicate that the sampler successfully excludes this material. As mentioned earlier, the gas flow rates from the sampler to the analyzer should be kept low in order to avoid excessive dilution of the sampled gas by the purge gas.

It should be noted that any number of gas species present in the containment volume 4 will back-diffuse, in amounts determined by the appropriate diffusion coefficients, into the sampler probe and ultimately to the analyzer. The sampler is not intended to be useful in the discrimination between equally diffusible gases.

The geometry of the sampler probe 3 in FIG. 2 may be altered widely. The barrier 7 may be a cylinder arranged concentrically within or without other cylinders comprising the sampler probe 3 body, or may be a flat plate. If a flat plate is employed it should be oriented with the ports facing downward in order to avoid the gravitational settling of large tramp particles on the ports.

While in the foregoing description and in the drawings there have been described a general invention and a specific embodiment, it should be understood that various changes and modifications of the invention may be made, especially in designing the invention for a specific application, without departing from the true spirit and scope of the invention, and that the foregoing should be interpreted as illustrative rather than limiting.

What is claimed is:

1. A sampler for gathering a sample of a gas from an environment containing an aerosol of tramp material in said gas which comprises:
   (a) a purge gas source;
   (b) a barrier having ports between two surfaces thereof, said ports adapted to permit back-diffusion of said sample of a gas therethrough, by virtue of said ports being of a size which is larger in diameter than one mean free path of molecules of said sample gas;
   (c) a sampler probe supporting said barrier such that a first surface of said surfaces of said barrier is presented to said environment and said sampler probe further defining a chamber with said barrier adapted to receive and channel flow of purge gas from said purge gas source over a second surface of said surfaces of said barrier such that a portion of the said purge gas flow passes through said ports in said barrier thereby inhibiting clogging of said ports by said aerosol of tramp material in said gas and the remaining portion of the purge gas flow gathers such amount of sample gas in said chamber as has back-diffused through said ports across said barrier; and
   (d) an analyzer adapted to receive the purge gas flow from said sampler probe, the purge gas flow containing additionally such amount of the sample of said gas as has back-diffused across said barrier.

2. The sampler of claim 1 wherein said ports are drilled holes.

3. The sampler of claim 1 wherein the said ports are pores in a naturally gas-permeable barrier material.

* * * * *